United States Patent [19]

Stephens

[11] 4,178,939

[45] Dec. 18, 1979

[54] VISUAL INDICATOR FOR CUFF-TYPE CATHETER

[75] Inventor: Thomas P. Stephens, Boxford, Mass.

[73] Assignee: Portex, Inc., Wilmington, Mass.

[21] Appl. No.: 838,026

[22] Filed: Sep. 29, 1977

[51] Int. Cl.² .......................................... A61M 25/00
[52] U.S. Cl. .............................. 128/207.15; 116/266; 116/DIG. 8; 128/349 B
[58] Field of Search ................. 128/207, 208, 348–351; 116/34 R, 114 PV, DIG. 8, 266

[56] References Cited

U.S. PATENT DOCUMENTS

| | | | |
|---|---|---|---|
| 3,407,817 | 10/1968 | Galleher | 128/351 |
| 3,625,199 | 12/1971 | Summers | 128/2 R |
| 4,016,885 | 4/1977 | Bruner | 128/349 B |
| 4,018,231 | 4/1977 | Wallace | 128/351 |

*Primary Examiner*—Dalton L. Truluck
*Attorney, Agent, or Firm*—Pollock, Vande Sande & Priddy

[57] ABSTRACT

Apparatus for visually indicating the degree of inflation of an inflatable cuff surrounding a catheter which is adapted to be inserted into a body passageway. The apparatus comprises a hollow-walled tubular member formed with a plurality of ridges and valleys and is selectively inflatable into a balloon-like shape in response to the pressure of air applied to the cuff by means of a passageway extending into the tubular member. The member is collapsible without occluding the fluid passageway extending into the indicator apparatus and thus without preventing the deflation of the cuff.

7 Claims, 7 Drawing Figures

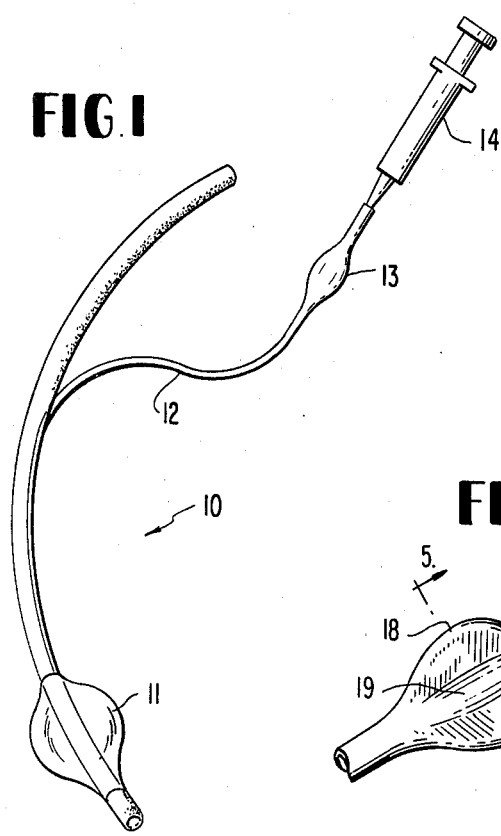
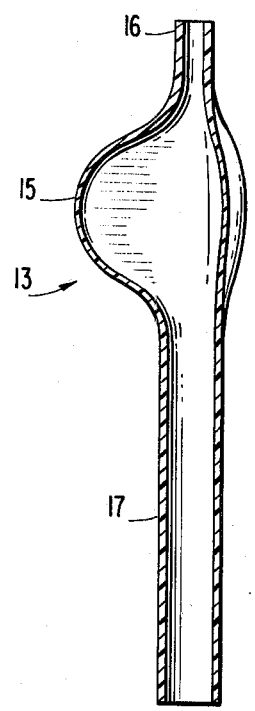
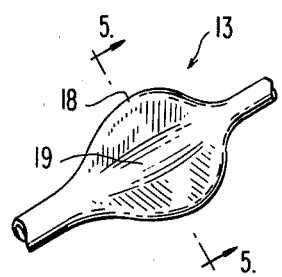
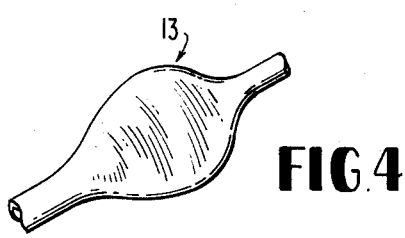
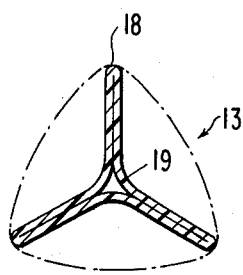
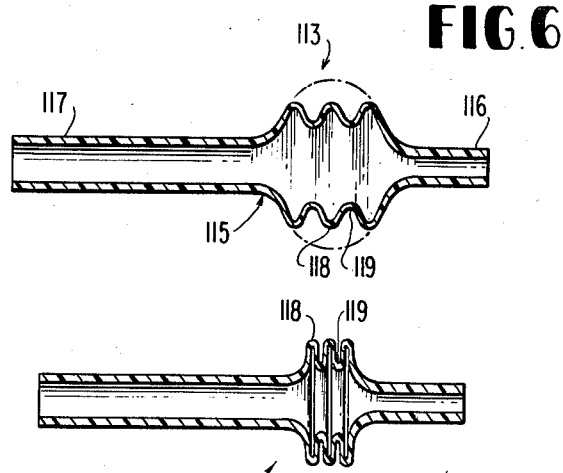

VISUAL INDICATOR FOR CUFF-TYPE CATHETER

BACKGROUND OF THE INVENTION

When a cuff-type catheter is inserted into a body passageway, such as a trachea, the cuff is expanded by pressurized fluid so as to block the passage of aspirated air past the cuff. A visual pressure indicator positioned in the fluid-flow passage visually indicates when the cuff is in the expanded position.

Known pressure indicators such as U.S. Pat. No. 4,018,231 issued Apr. 19, 1977 require an additional closed central tubular passageway extending through the indicator to ensure that the pressurized air in the cuff can be withdrawn to collapse the cuff when a negative pressure has collapsed the walls of the indicator about the central passageway. This additional tube is costly to manufacture in relation to the price of the indicator and is itself subject to blockage if accidentally deformed. U.S. Pat. No. 4,016,885 issued Apr. 12, 1977 discloses a hollow circular tubular pressure indicator wherein the opposite sides of the indicator inherently collapse into abutting relation when vacuumized which may block the passageway through the indicator.

SUMMARY OF THE INVENTION

Thus, an object of the invention is to provide a visual pressure indicator which is formed with a single hollow tubular passageway that is inflatable and collapsible without blocking the fluid-flow passage through the indicator.

Another object of the present invention is to provide a visual pressure indicator which is both easy to manufacture and install in the fluid-flow passage between a source of pressurized fluid and an inflatable cuff.

The pressure indicating apparatus of the present invention includes a hollow, thin-walled tubular passageway which is initially formed to include a plurality of ridges and valleys which, when pressurized, will inflate into a balloon-like shape visually indicative of the inflation of the cuff within the body passageway. When vacuumized, the ridges and valleys will deflate without occluding the fluid-flow passage through the indicator.

In a preferred embodiment, an odd number of ridges and valleys extend longitudinally along the wall of the indicator and are positioned such that the collapse of said indicator will bring the valleys into abutting contact without occluding the fluid passageway through the indicator.

In a further preferred embodiment, the ridges and valleys extend circumferentially about the longitudinal axis of the indicator, forming a bellows-like shape when not inflated. The tubular passageway inflates into a balloon-like shape in response to an increase in pressure and deflates to its initial shape when vacuumized without occluding the fluid-flow passage extending through the indicator.

BRIEF DESCRIPTION OF THE DRAWINGS

Further characteristics and advantages of the invention appear with reference to the accompanying drawings in which:

FIG. 1 shows a catheter assembly including an attached cuff, tubular passageway, visual pressure indicator and pressure source;

FIG. 2 shows a cross-sectional view of a preferred embodiment of the visual pressure indicator;

FIG. 3 shows a perspective view of the visual pressure indicator of FIG. 2 in a non-inflated or initial state;

FIG. 4 shows a perspective view of the visual indicator of FIG. 3 in an inflated state;

FIG. 5 shows a cross-sectional view of the pressure indicator of FIG. 2 in a fully collapsed state;

FIG. 6 shows a cross-section of a further preferred embodiment of the visual pressure indicator in a non-inflated or initial state;

FIG. 7 shows a cross-section of the indicator of FIG. 6 in the fully collapsed state.

DETAILED DESCRIPTION OF THE PREFERRED EMBODIMENT

Referring now to the drawings, there is shown in FIG. 1, generally at 10, a cuff-type catheter which is insertable into a body passageway, such as a trachea. The catheter 10 may take the form of either an endotracheal tube or a tracheostomy tube. An inflatable cuff 11 surrounds and is attached to a portion of the catheter 10 which is insertable into the body passageway, with the cuff 11 being inflatable to block the passage of air through the body passageway externally of the tube. A thin-walled tubular passageway 12 extends from the cuff 11 to a visual pressure indicator 13 located outside the body passageway. The indicator 13 is further connected to a source of pressurized fluid 14, such as air.

The inflatable cuff 11 has an initially collapsed shape when the catheter 10 is first inserted into the body passageway. After positioning the catheter 10 in the body passageway, pressurized fluid is injected by pressure source 14 through indicator 13 and tubular passageway 12 to inflate cuff 11. To remove the catheter 10 from the body passageway, a negative pressure or vacuum is generated by pressure source 14 to draw the pressurized air from the cuff 11 through tubular passageway 12 and visual pressure indicator 13. The cuff 11 then collapses into its initial shape, allowing the catheter 10 to be removed from the body passageway. The collapse of cuff 11 is visually indicated by a corresponding collapse of indicator 13 which is visible to the medical attendant.

With reference to FIGS. 2-7, the visual pressure indicator 13 comprising the present invention will be discussed in detail.

A preferred embodiment of the visual pressure indicator 13 is shown in FIGS. 2-5. The indicator 13 comprises a hollow thin-walled tubular passageway 15. A first tubular end 16 of indicator 13 attaches to the hollow tubular passageway 12, while a second tubular end 17 of indicator 13 attaches to the pressure source 14.

The thin-walled tubular passageway 15 is formed with a plurality of longitudinally extending interconnected ridges 18 and corresponding valleys 19, which are visually apparent when indicator 13 is in a non-inflated state. For reasons that will become apparent later, the tubular passageway 15 is preferably formed with an odd number of ridges 18 and corresponding valleys 19.

The tubular passageway 15 may be formed of polyvinyl chloride, rubber or a like material, and the ridges 18 and valleys 19 may be initially formed by a known extrusion molding process, wherein a hollow tube of polyvinyl chloride or the like is positioned within a mold of the desired shape, heated and deformed into the shape of the mold by injecting pressurized fluid through the hollow tubular passageway. The extrusion molding process in itself forms no part of the present invention.

The wall of passageway 15 is stretched during the molding process and is relatively thinner than the walls forming the ends 16 and 17 of indicator 13. This allows the ridges 18 and valleys 19 to deform relative to the ends 16 and 17 in response to the change in pressure within passageway 15.

When it is desired to remove the catheter 10 from the body passageway, a negative pressure or vacuum is generated by pressure source 14 to draw the air from cuff 11 through tubular passageway 12 and indicator 13, thereby collapsing cuff 11 and allowing catheter 10 to be withdrawn from the body passageway.

The valleys 19 of tubular passageway 15 collapse into abutting contact with one another under the negative pressure generated by pressure source 14. Because an odd number of valleys 19 are initially formed in the wall of passageway 15, the collapsed valleys 19 abut without occluding the fluid-flow passage through indicator 13, as shown in FIG. 5. The odd number of ridges 18 and valleys 19 ensure that during complete collapse of the passageway 15, all of the air injected into cuff 11 can be withdrawn through indicator 13. If an even number of ridges 18 and valleys 19 were initially formed in tubular passageway 15 of the indicator 13, the valleys 19 would symmetrically collapse into an abutting relationship under negative pressure and block the fluid-flow passageway through indicator 13, preventing complete collapse of cuff 11.

Although the drawings show only three interconnected ridges 18 and valleys 19 formed in tubular passageway 15, it is within the scope of the invention to form the tubular passageway 15 with any odd number of interconnected ridges 18 and corresponding valleys 19 greater than three.

Indicator 13 of the present invention, unlike the prior art, does not need a separate tubular passageway extending therethrough to ensure complete collapse of cuff 11. The hollow thin-walled tubular passageway 15 of the present invention ensures an open fluid-flow passage at all times.

A further preferred embodiment of the invention is shown in FIGS. 6 and 7, wherein similar numerals are used for similar elements preceded by the numeral 1.

Indicator 113 includes a hollow tubular passageway 115 comprising circumferential ridges 118 and corresponding valleys 119, forming a bellows-like shape when indicator 113 is in the non-inflated state as shown in FIG. 6. A first tubular end 116 of passageway 115 attaches to a tubular passageway 112 which, in turn, is connected to a cuff (not shown). A second tubular end 117 of indicator 113 attaches to a pressure source 114.

The tubular passageway 115 may be formed of polyvinyl chloride, rubber or a like material, and the circumferential ridges 118 and corresponding valleys 119 may be formed by a known extrusion molding process, wherein a hollow tube of polyvinyl chloride or the like is positioned within a mold of a desired shape, heated and deformed by inserting pressurized fluid through the hollow tubular passageway. The extrusion molding process comprises no part of the present invention. The wall of passageway 115 is stretched during the molding process and is thinner than the walls forming ends 116 and 117, which allows the interconnected ridges 118 and valleys 119 to deform relative to the ends 116 and 117 in response to a change in pressure within passageway 115.

When pressurized air is inserted through indicator 113, the ridges 118 and valleys 119 inflate into a balloon-like shape visually indicative of the inflation of cuff 111 within the body passageway. A negative pressure generated by source 114 collapses tubular passageway 115 into its initial bellows-like shape without occluding the fluid-flow passageway through indicator 113. The indicator 113 of the present invention does not need a separate tubular passageway extending therethrough to ensure complete collapse of cuff 111.

The embodiments described in the foregoing specification and shown in the drawings are to be regarded as non-limiting examples, which can be altered and completed in any way within the scope of the invention.

What I claim is:

1. A deformable apparatus for visually indicating the shape of an inflatable cuff that surrounds a surgicomedico catheter and the like of the type adaptable for insertion into a body passage, and comprising:
   a deformable, hollow-walled indicator enclosing a substantially empty, chamber-like area and including first and second apertures each extending through a wall portion thereof;
   a tubular-connecting member including a first end portion in fluid-tight engagement with a wall portion forming said first aperture, said tubular member further including a second end portion in fluid-tight engagement with said inflatable cuff to provide a continuous, fluid-tight passageway between the chamber of said indicator and said cuff;
   fluid pressure means in fluid-tight engagement with a wall portion forming said second aperture for selectively varying the fluid pressure within said continuous, fluid-tight passageway to inflate and deflate said indicator and said cuff, respectively; and
   preformed deformable ridge means extending substantially longitudinally along substantially the length of said hollow-walled indicator for controlling the configuration of said indicator responsive to selective actuation of said fluid pressure means, said ridge means being present in odd numbered multiples thereof preventing occlusion of said indicator chamber during deflation of said cuff.

2. Apparatus according to claim 1, wherein said deformable ridge means comprises the hollow wall of said indicator being formed with a plurality of substantially longitudinally extending interconnected ridges and corresponding valleys that are circumferentially spaced about the indicator;
   said ridges and corresponding valleys being expandable into a substantially balloon-like configuration when pressurized fluid is introduced into said continuous fluid-tight passageway;
   and said ridges and corresponding valleys being collapsible without occluding said indicator chamber when said continuous fluid-tight passageway is selectively vacuumized.

3. Apparatus according to claim 2, wherein said substantially longitudinally extending ridges and corresponding valleys are visually apparent in the wall of said hollow-walled indicator when said indicator is in a non-inflated state.

4. Apparatus according to claim 2, wherein a valley is positioned between each pair of adjacent ridges and an identical, odd number of ridges and corresponding valleys are formed in the hollow wall of said indicator;

with said odd number of ridges and corresponding valleys collapsing when selectively vacuumized by said first means to form a central fluid-flow passage through said indicator chamber to prevent occlusion of said indicator.

5. Apparatus according to claim 2, wherein the wall portion of said indicator comprising said ridges and corresponding valleys is of less width than the wall portions of said indicator engaging said fluid pressure means and said tubular connecting member, to allow said ridges and corresponding valleys to deform with respect to the remaining portion of said indicator in response to selective actuation of said fluid pressure means.

6. Apparatus according to claim 1, wherein said hollow-walled indicator is formed of polyvinyl chloride.

7. Apparatus according to claim 4, wherein at least three circumferentially spaced ridges and three corresponding, circumferentially spaced valleys are formed in the hollow wall of said indicator assembly.

* * * * *